United States Patent
Al-Zahrani et al.

(10) Patent No.: US 6,541,418 B1
(45) Date of Patent: Apr. 1, 2003

(54) CATALYST SYSTEMS FOR THE OXIDATIVE DEHYDROGENATION OF HYDROCARBONS

(75) Inventors: Saeed M. Al-Zahrani, Riyadh (SA); Ahmed E. Abasaeed, Riyadh (SA); Nimir O. Elbashir, Riyadh (SA); Mazhar A. Abdulwahed, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 201 days.

(21) Appl. No.: 09/722,093

(22) Filed: Nov. 22, 2000

(51) Int. Cl.⁷ .................................................. B01J 23/20
(52) U.S. Cl. ....................... 502/354; 502/335
(58) Field of Search ................. 502/335, 337, 502/354, 355

(56) References Cited

U.S. PATENT DOCUMENTS

| | | |
|---|---|---|
| 3,770,812 A | 11/1973 | Blood |
| 5,220,049 A | 6/1993 | Honda et al. |
| 5,468,710 A | 11/1995 | Resasco et al. |
| 5,595,719 A | 1/1997 | Ul-Haque et al. |
| 5,599,517 A | 2/1997 | Ul-Haque et al. |
| 5,759,946 A | 6/1998 | Hoang et al. |

FOREIGN PATENT DOCUMENTS

| | | |
|---|---|---|
| DE | 2030 699 | 1/1971 |

OTHER PUBLICATIONS

Derwent Database, Abstract of German Pat. No. 2124438, Jan. 1972.
Derwent Database, Abstract of European Pat. Publication No. 557790, Sep. 1993.
Derwent Database, Abstract of Japanese Pat. No. 3218327, Sep. 1991.
Derwent Database, Abstract of Japanese Pat. No. 7010782, Jun. 1993.

*Primary Examiner*—Stanley S. Silverman
*Assistant Examiner*—Edward M. Johnson
(74) *Attorney, Agent, or Firm*—Kramer Levin Naftalis & Frankel

(57) ABSTRACT

A new catalyst system is disclosed for the production of olefins through oxidative dehydrogenation of hydrocarbons. The catalyst system having the atomic ratios described by the empirical formula $Bi_a Ni\ O_b / Al_2 O_3$.

2 Claims, No Drawings

CATALYST SYSTEMS FOR THE OXIDATIVE DEHYDROGENATION OF HYDROCARBONS

RELATED APPLICATION

This application claims priority from European patent application Ser. No. 99123447.7 filed Nov. 24, 1999. Each of the foregoing applications and patents, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

FIELD OF THE INVENTION

The present invention provides catalysts for oxidative dehydrogenation of hydrocarbons. It is directed to new catalyst system exhibiting very high olefin selectivity.

A number of oxidative dehydrogenation catalysts are known in this field such as U.S. Pat. Nos. 5,759,946 and 5,468,710; Japanese Patent Nos. 93150371, 07010782 A2 and 3-218327; German Patent No. 2, 124,438; and EP Patent No. 0557790 A2.

BACKGROUND OF THE INVENTION

Olefinic hydrocarbons are very important intermediates in the petrochemical industry. Examples of commercial production interests include ethylene, propylene, butenes, isobutene, and styrene. Substantial efforts were directed towards the production of such compounds by conventional catalytic dehydrogenation. Conventional dehydrogenation has several disadvantages, such as the need of high reaction temperature (600–800° C.), the catalyst deactivation by coke formation, the consequent need of periodic catalyst regeneration, and the thermodynamic limitation of the catalyst activity. These drawbacks can be avoided in the case of oxidative dehydrogenation (ODH), due to the presence of oxygen in the reaction mixture. However, to date there is no commercial catalyst system available for this purpose.

U.S. Pat. No. 5,468,710, relates to a composition containing sulfided nickel and non-acidic alumina and used as a normal dehydrogenation catalyst of organic compounds, e.g., isobutane to give isobutene.

Isobutene and methacrolein were prepared according to the JP 07010782 A2 by treatment of isobutane with molecular oxygen in the gas phase in the presence of oxidative dehydrogenation catalyst mainly containing Mo and Bi. Isobutane, oxygen and nitrogen gas mixture was passed through a reactor containing mixed oxide catalyst of molybdenum, bismuth, iron, cobalt, cesium and silicon and oxidative dehydrogenation catalyst containing nickel and phosphorous at 440° C. to show 3.8% conversion and 13.9, 3.3 and 18.9% selectivity for isobutene, propene, and methacrolein, respectively.

Japanese Patent No. 93150371 relates to alkali metals and alkaline earth metals containing catalysts were used for preparation of isobutene and methacrolein from isobutane with oxidative dehydrogenation catalysts and mixed oxide catalysts containing bismuth and molybdenum.

German Patent No. 2,124,438 relates to an oxidative dehydrogenation of isobutane in the presence of hydrogen iodide. The conversion of isobutane was 28% and the selectivity to isobutene was 85%. The method, however, has the disadvantage of requiring the addition of hydrogen iodide.

The Japanese Patent relates to an oxidative dehydrogenation of propane or isobutane using a catalyst comprising tin oxide and phosphorous oxide as the main components. It also relates to a catalyst having indium oxide and phosphorous oxide as the main components. However, the selectivity is low; 32% at 1.4 conversion.

U.S. Pat. No. 5,759,946 relates to a catalyst based on chromium oxide for oxidative dehydrogenation of hydrocarbons.

EP Pat. No. 0557790 A2 relates a catalyst containing phosphorous oxide for producing isobutene by oxidative dehydrogenation of isobutane.

As seen from the above, it is a major challenge to achieve high conversion to olefin at high selectivity, i.e., to achieve maximum yield of the desired product, while minimizing the further oxidation activity. None of the cited references teaches or discloses a catalyst, which provides a high performance of the selective production of olefins from their corresponding paraffins. Accordingly, it would be desirable to produce an improved catalyst for use in the selective production of olefins from their corresponding paraffins.

OBJECTS OF THE INVENTION

It is an object of this invention to overcome the difficulties presented in the cited references for producing olefins as disclosed in the present application.

Another object of the invention is to provide a useful catalyst for producing olefins from hydrocarbons selectively by performing the oxidative dehydrogenation in the presence of a catalyst comprising bismuth, nickel and alumina.

The foregoing and other objects and advantages of the invention will be set forth in or will become apparent from the following description.

SUMMARY OF THE INVENTION

The present invention provides a new catalyst system comprising bismuth, nickel and alumina for the production of olefins by the oxidative dehydrogenation of hydrocarbons. The reaction can be carried out at low reaction temperature with no partial oxidation product formation. Such high selective catalyst may also find further application in the catalytic separation of hydrocarbons or in synergistic combinations with other reactions.

The catalyst including a catalytic composition having the atomic ratios described by the empirical formula set forth below:

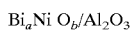

$Bi_a Ni\ O_b/Al_2O_3$

Where: a=0.001 to 0.5 b=the number of oxygen required to satisfy the valency requirements of the elements present The numerical values of a and b represent the relative gram-atom ratios of the elements, respectively, in the catalyst composition, where b is a number required to satisfy the valence requirements of the other elements. The elements are present in combination with oxygen, preferably in the form of various oxides. Other objects as well as aspects, features and advantages of the present invention will be apparent from a study of the present specification, including the claims and specific examples.

DETAILED DESCRIPTION OF THE PRESENT INVENTION

One aspect of the invention teaches to a new catalytic system for the production of olefins from hydrocarbons via the oxidative dehydrogenation, in particular, for the production of isobutene from isobutane. More specifically, the present invention is directed to a highly selective catalyst comprising the atomic catalyst composition described by the empirical formula set forth below.

$$Bi_aNiO_b/Al_2O_3$$

Where: a=0.001 to 0.5
b=the number of oxygen required to satisfy the valency requirements of the elements present The catalyst of this invention is supported on alumina. However, other suitable supports including silica, titania, zirconia, zeolites, silicon carbides and others alone or as mixture can be used. The catalyst comprises usually 70–98% by weight alumina.

CATALYTIC OXIDATIVE DEHYDROGENATION

The following examples are illustrative of some of the products and methods of making and using the same falling within the scope of the present invention. They are, of course, not to be considered in any way limitative of the invention. Numerous changes and modifications can be made with respect to the invention. Illustrative examples were made for production of isobutene from isobutane.

The basic catalyst of the present invention is a mixed metal oxide catalyst, which could be prepared according to any procedure well known by a skilled person in the art. Methods used to prepare representative catalyst are given below.

As used in the following examples, the following terms are defined in the following manner:
1. "W/F" is defined as the weight of the catalyst in grams divided by the flow rate of reactant stream in ml/sec measured at S.T.P.
2. "Isobutane (i-$C_4H_{10}$) conversion" is defined as:

$$\frac{\text{Mols i-}C_4H_{10} \text{ in feed} - \text{Mols i-}C_4H_{10} \text{ in effluent}}{\text{Mols i-}C_4H_{10} \text{ in feed}} \times 100\%$$

3. "Isobutene (i-$C_4H_8$) selectivity" is defined as:

$$\frac{\text{Mols i-}C_4H_8 \text{ in effluent}}{\text{Mols i-}C_4H_{10} \text{ converted}} \times 100\%$$

4. "Isobutene (i-$C_4H_8$) yield" is defined as:

$$\frac{\text{Mols i-}C_4H_8 \text{ formed}}{\text{Mols i-}C_4H_{10} \text{ in feed}} \times 100\%$$

The following conditions were employed:
reaction temperature: 250–450° C.
catalyst: 1 gm (2.1 cc)
pressure: atmospheric
W/F: 0.8 sec.
feed composition: isobutane/oxygen/helium: 26.5/6.6/66.9 (mol %)

CATALYST TEST

Calcined catalysts were pressed into pellets, then crushed to 20–40 mesh fraction. The catalysts were tested in fixed bed quartz reactor. In each test the catalyst was pretreated in a stream of a mixture of oxygen and helium for one hour at 400° C. Then, the feed gas was passed through the reactor at desired temperature.

After reaching the steady state, the reactor effluent was analyzed by using a modem gas chromatograph (HP 6890), equipped with both FID and TCD detectors. Activity results were calculated according to the equations given above.

EXAMPLE 1

The catalyst used in this example has the empirical formula of $Bi_{0.42}Ni/Al_2O_3$. It was prepared by dissolving the required amounts of nickel nitrate hexahydrate, and bismuth nitrate pentahydrate in 150 ml distilled water. Then alumina (Capital A, from CONDEA) was added to the mixture. The formed paste was then dried at 120° C., and calcined in air at 700° C. After calcination and pretreatment the catalyst was tested at 250° C. Results are summarized in Table 1.

EXAMPLES 2 and 3

The experimental procedures of Examples 2 and 3 were essentially the same as described for Example 1 with the exception that the reaction temperature was changed to 350° C. and 450° C., respectively. Results are given in table 1.

EXAMPLE 4

The catalyst used in this example has the empirical formula of $Bi_{0.28}Ni/Al_2O_3$. It was prepared by same method described in Example 1. After calcination and pretreatment the catalyst was tested at 250° C. Results are summarized in table 1.

EXAMPLES 5 and 6

The experimental procedures of Examples 5 and 6 were essentially the same as described for Example 4 with the exception that the reaction temperature was changed to 350° C. and 450° C. respectively. Results are given in table 1.

EXAMPLE 7

The catalyst used in this example has the empirical formula of $Bi_{0.07}Ni/Al_2O_3$. It was prepared by same method described in Example 1. After calcination and pretreatment the catalyst was tested at 250° C. Results are summarized in table 1.

EXAMPLES 8 and 9

The experimental procedures of Examples 5 and 6 were essentially the same as described for Example 7 with the exception that the reaction temperature was changed to 350° C. and 450° C. respectively. Results are given in table 1.

EXAMPLE 10

The catalyst used in this example has the empirical formula of $Ni/Al_2O_3$ It was prepared by same method described in Example 1 using nickel nitrate only. After calcination and pretreatment the catalyst was tested at 330° C. Results are summarized in table 1.

EXAMPLES 11 to 13

The experimental procedures of Examples 11 to 13 were essentially the same as described for Example 10 with the exception that the reaction temperature was changed to 380° C., 420° C. and 450° C. respectively. Results are given in table 1.

TABLE 1

Activity Results

| Example No. | T (° C.) | X (%) | i-$C_4H_8$ Y | S | $C_3H_6$ Y | S | $CO_x$ Y | S |
|---|---|---|---|---|---|---|---|---|
| 1 | 250 | 0.9 | 0.7 | 77.2 | 0.0 | 0.0 | 0.2 | 22.8 |
| 2 | 350 | 7.4 | 3.6 | 48.0 | 0.2 | 3.2 | 3.6 | 48.5 |
| 3 | 450 | 9.2 | 4.0 | 43.3 | 0.8 | 8.2 | 4.2 | 45.6 |
| 4 | 250 | 2.8 | 2.7 | 97.6 | 0.0 | 0.0 | 0.1 | 2.4 |
| 5 | 350 | 6.2 | 3.4 | 55.0 | 0.1 | 2.0 | 2.7 | 43.5 |
| 6 | 450 | 8.9 | 4.2 | 47.4 | 0.5 | 5.2 | 4.1 | 45.5 |
| 7 | 250 | 3.5 | 3.5 | 99.0 | 0.0 | 0.0 | 0.0 | 0.0 |
| 8 | 350 | 4.4 | 3.0 | 67.0 | 0.1 | 1.1 | 1.4 | 31.9 |
| 9 | 450 | 10.8 | 6.0 | 55.1 | 0.4 | 4.0 | 4.2 | 38.6 |
| 10 | 330 | 0.9 | 0.8 | 92.1 | 0.0 | 0.0 | 0.1 | 7.9 |
| 11 | 380 | 4.4 | 3.0 | 66.7 | 0.1 | 1.6 | 1.4 | 17.6 |
| 12 | 420 | 10.5 | 5.6 | 53.4 | 0.4 | 3.3 | 3.4 | 27.9 |
| 13 | 450 | 11.3 | 5.9 | 52.2 | 0.4 | 3.9 | 4.8 | 28.4 |

X i-$C_4H_{10}$-Conversion
Y Yield in mol %
S Selectivity in mol %
$CO_x$ Carbon dioxide and carbon monoxide As shown in the above table the nickel alumina appears to be a good for isobutane oxidative dehydrogenation (examples 10–13). By incorporating small amount of bismuth into this catalyst, activity and selectivity towards the desired isobutene, could be dramatically enhanced (examples 1 to 9). Thus, in example isobutane conversion and 99% selectivity for isobutene were obtained at 250° C. using a bismuth-nickel-alumina catalyst, while 0.9% conversion at 330° C. and 92% selectivity on the nickel-alumina catalyst (Example 10).

As seen from these results, nickel-alumina catalyst is suitable for the dehydrogenation reaction. The addition of bismuth to this catalyst improves carbon conversion, increases olefin selectivity, and lowers the reaction temperature.

The forgoing description of the preferred embodiments of the invention has been presented for purpose of illustration and obviously many modifications and variations are possible.

It is intended that the scope of the invention is defined by the claims appended hereto.

The features disclosed in the foregoing description and in the claims may, both separately and in any combination thereof, be material for realizing the invention in diverse forms thereof.

In this disclosure, "comprises," "comprising," and the like can have the meaning ascribed to them in U.S. Patent law and can mean "includes," "including," and the like.

These and other objects and embodiments of the invention are provided in, or are obvious from, the following detailed description.

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. A catalyst for the oxidative dehydrogenation of hydrocarbons comprising an alumina supported catalyst composition having the following empirical formula:

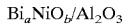

$Bi_aNiO_b/Al_2O_3$ where: a=0.001 to 0.5 b=the number of oxygen atoms required to satisfy the valency requirements of the elements Bi and Ni.

2. The catalyst of claim 1, wherein said alumina comprises 70–98% by weight of the catalyst composition.

* * * * *